| United States Patent [19] | [11] Patent Number: 4,835,264 |
| Liav et al. | [45] Date of Patent: May 30, 1989 |

[54] SYNTHESIS OF 3,6-DI-O-METHYL-D-GLUCOSE AND COMPOUNDS FORMED THEREBY

[75] Inventors: Avraham Liav; Mayer B. Goren, both of Denver, Colo.

[73] Assignee: National Jewish Center, Denver, Colo.

[21] Appl. No.: 940,857

[22] Filed: Dec. 12, 1986

[51] Int. Cl.$^4$ ............... C07G 3/00; C07G 11/00; C07H 15/00; C07H 17/00

[52] U.S. Cl. ................... 536/4.1; 536/18.5; 536/18.6

[58] Field of Search ............... 536/4.1, 18.5, 18.6

[56] References Cited

PUBLICATIONS

Fujiwara et al., *Infect. Immun.* 43:245–252 (1984).

Owen et al., *J. Chem. Soc.* (1941):339–344.

*Primary Examiner*—Ronald W. Griffin
*Attorney, Agent, or Firm*—Felfe & Lynch

[57] ABSTRACT

A new method for the production of 3,6-Di-O-methyl-D-glucose is presented.

12 Claims, No Drawings

SYNTHESIS OF 3,6-DI-O-METHYL-D-GLUCOSE AND COMPOUNDS FORMED THEREBY

FIELD OF THE INVENTION

This invention relates to a method of synthesizing the compound 3,6-DI-O-methyl-D-glycose.

BACKGROUND OF THE ART 3,6,-Di-O-methyl-D-glucose has recently been recognized, isolated, and purified from specimens of *Mycobacterium leprae*, the vector for human leprosy [Brennan, et al., *Int. J. Lepr.* 48: 382-387 (1980); Hunter, et al., *J. Bacteriol* 147: 728-735 (1981); Hunter, et al., *J. Biol. Chem.* 257: 15072-15078 (1982); Tarelli, et al., *Carbohydr. Res.* 131: 346-352 (1984)]. This methylated sugar is a part of a phenolic glycolipid, known as PGL-I to those in the art. The lipid molecule contains a diacylated phenol phthiocerol, which is the definitive structural feature of certain "mycosides." "Mycosides," as used herein, refers to a group of glycoside containing molecules characteristic of several mycobacterial species [Asselineau, et al., *Annales de Microbiologie* 129: 46-69 (1978)]. PGL-I iss, however, distinct from all other similar mycosides in that its phenolic hydroxyl is glycosidically linked to a unique trisaccharide. This trisaccharide confers highly specific antigenic and serological activity to the lipid "backbone," which is generally inert.

The art recognizes that glycolipids may be used as serological diagnostic test reagents. Many tumor specific antigens are glycolipids. Further, and of specific interest to the invention described infra, is the efficacy of PGL-I as a reagent useful in recognizing leprosy infection or disease [Payne, et al., *Int. J. Lepr.* 50: 220-221]. The more specific phenolic glycolipid-I can be employed, e.g., in connection with enzyme linked immunosorbent assays (ELISAs), immunoenzymometric assays (IEMAs), radioimmunoassays (RIAs) or any of the diagnostic methods currently in use which involve detection or estimation of antibodies. PGL-I has been recognized as useful for detecting humoral antibodies specific for the contained haptenic di- or tri-saccharide moieties, Gigg, et al., *Chem. Phys. Lipids* 38: 299-307 (1985); Fujiwara, et al., *Infect. Immun.* 43: 245-252 (1984). Glycoconjugates of these with bovine serum albumin (BSA) have been prepared and used for this purpose (Fujiwara, supra). The rarity of PGL-I as a naturally occurring compound, as well as the obvious difficulty and expense of obtaining it in sufficient quantities for diagnostic assays, have, therefore, served as a stimulus for deriving methods of synthesizing the compound or of satisfactory alternatives. These include derivatives of the entire trisaccharide, the terminal disaccharide and even of the terminal 3,6-di-O-methyl glucose which is the principal specific antigen of the trisaccharide moiety (Fujiwara et al., supra).

Several synthesis methods for this methylated glucose are known to the art. Bell, et al., *J. Chem. Soc.* (1936): 1553-1554, pioneered in this regard by treating 1,2,0-isopropylidene-3-0-methyl-6-0-p-tolylsulfonyl-α-D-glucofuranose with sodium methoxide, as well as by methylation of 1,2,0-isopropylidene-α-D-glucofuranose-5-nitrate. Both syntheses gave intermediates that were readily converted into the 3,6-di-O-methylglucose. Gigg, et al., *J. Chem. Soc.* pp. 82-86 (1966), methylated 5-0-benzyl-1,2,-0-isopropylidene-D-glucofuranose to provide another such intermediate. Most recently, Gigg, et al., *Chem. Phys. Lipids* 38: 299-307 (1985), synthesized the compound from 5-0-allyl-1,2-0-isopropylidene 3-0-methyl-α-D-glucofuranose.

Each of these synthesis methods is complex, expensive, and involves numerous steps. The method described herein presents a simpler, more practical method, using readily available D-glucurono-6,3-lactone as the starting substance.

DETAILED DESCRIPTION OF PREFERRED EMBODIMENTS

The reaction described herein starts with D-glucurono-6,3-lactone, (1):

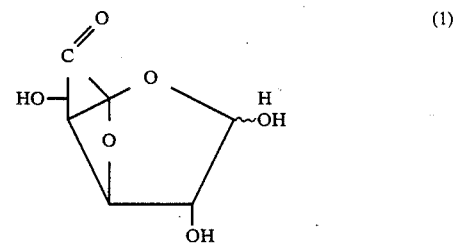

being converted into its crystalline 1,2,-0-isopropylidene derivative (1,2-0-Isopropylidene-α-D-glucofuranurono-6,3-lactone) as earlier described by Owen, et al., *J. Chem. Soc.* (1941): 339-344.:

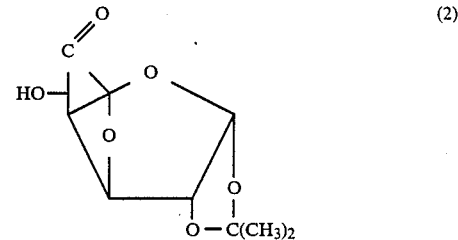

This product is blocked (at OH-5) by treatment with either dihydropyran or with methyl vinyl ether in methylene chloride in the presence of pyridinium-p-toluene sulfonate, to obtain the two acetal derivatives (3) or (4) respectively:

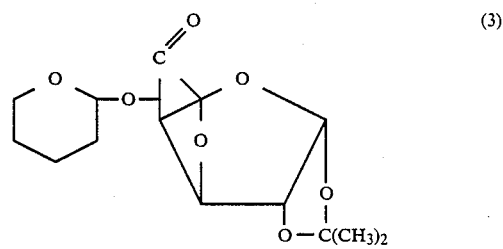

(1,2-0-Isopropylidene-5-0-(tetrahydropyran-2-yl)-α-D-glucofuranurono-6,3-lactone); and

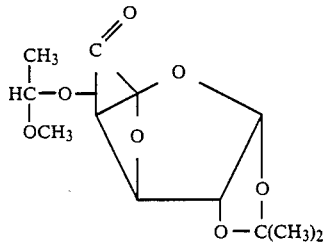

(1,2-0-Ispropylidene-5-0-(1-methoxyethyl)-α-D-glucofuranurono-6,3-lactone).

The 5-0-(tetrahydropyran-2-yl) derivative (3) is treated with LiAlH₄ to obtain 1,2-0-Isopropylidene-5-0-(tetrahydropyran-2-yl)-α-D-glucofuranose, i.e.:

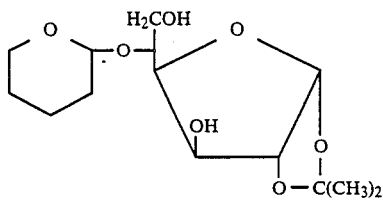

Alternatively, the derivative 1,2-0-Isopropylidene-5-0-(1-methyoxyethyl)-α-D-glucofuranose (6):

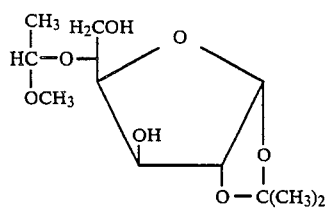

is obtained as well, when (4) is treated as described supra.

When (5) is treated with CH₃I and sodium hydride, the compound 1,2-0-Isopropylidene-3,6-di-O-methyl-5-0-(tetrahydropyran-2-yl)-α-D-glucofuranose (7):

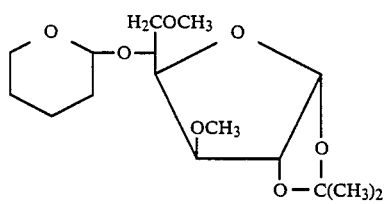

is derived.

Similarly, (6) is converted into 1,2-0-Isopropylidene-5-0-(1-methoxyethyl)-3,6-di-O-methyl-α-D-glucofuranose (8):

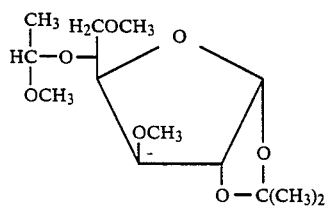

Acid hydrolysis, of (7) followed by neutralization, yields (9):

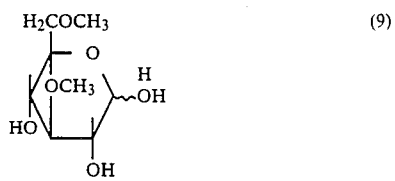

which is 3,6-di-O-methyl-D-glucose.

Compound (9) is obtained as well by treating (8) in the same manner as (7).

Acetylation of (9) produces the 1,2,4 tri-O-acetyl derivative whose ¹H-NMR spectrum was identical with that of an authentic sample prepared from 3,6-di-O-methyl glucose synthesized according to the prior art (Bell supra).

EXAMPLE

D-glucurono-6,3-lactone was converted into its crystalline 1,2-0 isopropylidene derivative (2). Blocking of OH-5 of this derivative by treatment with either dihydropyran or methyl vinyl ether in methylene chloride in the presence of pyridinium p-toluenesulfonate (1 hour at room temperature) gave the desired results: both acetal derivatives were isolated in high yield following a short chromatography on silica gel. Compound (3) was obtained in 95% yield $[\alpha]_D^{24}+52°$ (c 1.0, chloroform)], and compound (4) in 87% yield $[\alpha]_D^{24}+64°$ (c 1.0, chloroform)]. The 5-0-(tetrahydropyran-2-yl) derivative (3) was reduced with LiAlH₄ in ether (boiling under reflux, 1 hour) to give the product (5) which in thin layer chromatography appeared as a mixture of two components. Separation of the two products (by chromatography on silica gel) is feasible but is not necessary: it is found that both products give 3,6-di-O-methyl-D-glucose as described infra. It appears that these two products are probably diastereoisomeric at C-2 of the tetrahydropyranyl moiety. This mixture was obtained in 86% yield after a short purification on silica gel (the product was eluted with ethyl acetate-hexane 3:2). $[\alpha]_D^{24}-14°$ (c 1.0, chloroform). The 5-0-(1-methoxyethyl) derivative (6) also appeared as a mixture of two components in thin layer chromatography and was isolated in 84% yield as the diastereoisomeric mixture; $[\alpha]_D^{24}-15°$ (c 1.0, chloroform).

Treatment of (5) (the mixture of the two isomers) with methyl iodide and sodium hydride (oil dispersion) in dimethyl formamide (DMF) (room temperature, 30 minutes) gave the 3,6-di-O-methyl derivative (7) which appeared as one spot in thin layer chromatography. A brief chromatography on silica gel (with hexane-ethyl acetate 3:2 as the eluant) removed residual oil and the syrupy (7) was isolated in 89% yield: $[\alpha]_D^{24}-16.5°$. In a similar manner the reduction product (6) was converted into the syrupy 3,6-di-O-methyl acetal (8) (87% yield: $[\alpha]_D^{24}-45°$ (0.5, chloroform). Acid hydrolysis (1% aqueous sulfuric acid, 1 h, 85° C.) of (7), followed by neutralization with barium carbonate gave 3,6-di-O-methyl-D-glucose (9) as the sole product. Chromatography on silica gel (in order to remove residual salts) gave the pure 3,6-di-O-methyl-D-glucose (9) (eluted with chloroform-methanol 9:1) in 92% yield (homogeneous syrup). It was crystallized from ethyl acetate: m.p. 118°–120°; $[\alpha]_D^{24}+93°$ (5 min.)→+63° (in water at equilibrium); [(D. S. Bell, supra) m.p. 113°–115°, $[\alpha]_D^{20} +61.5°$ (in water at equilibrium); [(Gigg et al, 1985, supra; m.p. 114°–116°, $[\alpha]_D^{24} +60°$ (final value)]. Compound (9) has the same mobility in tlc (in benzene-methanol 3:1) as an authentic sample of 3,6-di-o-methyl-D-glucose prepared by one of the already known procedures (Bell, supra). Also, gas chromatography of O-trimethylsilyl derivatives showed it to be identical with 3,6-di-O-methyl-D-glucose. The per-O-trimethylsilyl derivative of the crystalline (m.p. 118°–120°) product described supra gave a minor peak (4.3 min) and a single major peak (4.7 min) in gas chromatography (2 mm diam., 6 ft. column of SE 30 at 150°, $N_2$ carrier gas at 30 ml/min). Trimethylsilylation of the product contained in the mother liquor gave a product mixture exhibiting two minor peaks (3.1 and 4.2 min) and two substantially equal major peaks at 4.8 and 5.5 min. When the crystalline product was briefly equilibrated in aqueous solution with a trace of pyridine, evaporated dry and the per-O-TMS derivative prepared, all four peaks seen in the mother liquor product were now distinguished: 3.2, 4.1 (both minor), 4.8 and 5.5 min very large and equally intense. The minor peaks may be due to $\alpha$ and $\beta$-O-TMS furanose forms, while the major peaks may be anomeric pyranose forms. In a similar manner, compound (8) was converted into 3,6-di-O-methyl-D-glucose in 92% yield (it has the same physical properties as described supra).

Acetylation of (9) gave the tri-O-acetyl derivative, the $^1$H-nmr spectrum of which was identical with the spectrum of an authentic sample of 1,2,4-tri-O-acetyl-3,6-di-O-methyl-D-glucose.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

We claim:

1. A method for producing 3,6-di-O-methyl-D-glucose comprising converting D-glucurono-6,3-lactone into its 1,2-0-isopropylidene derivative, treating said isopropylidene derivative to obtain acetal derivatives thereof, reducing said acetal derivatives, treating the reduction products to form methyl derivatives thereof, and subjecting said methyl derivatives to acid hydrolysis under conditions favoring formation of 3,6-di-O-methyl-D-glucose.

2. A method as in claim 1, wherein said isopropylidene derivative is blocked at 5-OH with a compound selected from the group consisting of dihydropyran and methyl vinyl ether to obtain acetal derivatives, reducing said acetal derivatives with $LiAlH_4$, treating said reduction derivatives with $CH_3I$ and sodium hydride to obtain methyl derivatives, and subjecting said methyl derivatives to acid hydrolysis and neutralization.

3. A compound of the formula

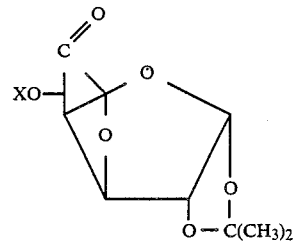

where X is tetrahydropyran-2-yl or 1-methoxyethyl.

4. Compound of claim 3, where X is tetrahydropyran-2-yl.

5. Compound of claim 3, where X is 1-methoxyethyl.

6. A compound of the formula

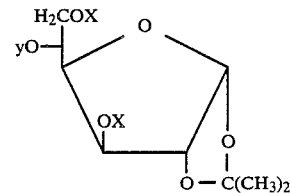

where X is hydrogen or methyl, and y is tetrahydropyran-2-yl or 1-methoxyethyl.

7. Compound of claim 6, where X is hydrogen.

8. Compound of claim 6, where X is methyl.

9. Compound of claim 6, where y is tetrahydropyran-2-yl.

10. Compound of claim 6, where y is 1-methoxyethyl.

11. Compound of claim 7 where y is tetrahydropyran-2-yl.

12. Compound of claim 7, where y is 1-methoxyethyl.

* * * * *